United States Patent [19]

Misaki et al.

[11] 4,275,161

[45] Jun. 23, 1981

[54] PROCESS FOR THE MANUFACTURE OF L-α-GLYCEROPHOSPHATE OXIDASE

[75] Inventors: Hideo Misaki; Yoshifumi Horiuchi; Kazuo Matsuura; Saburo Harada, all of Shizuoka, Japan

[73] Assignee: Toyo Jozo Kabushiki Kaisha, Shizuoka, Japan

[21] Appl. No.: 59,583

[22] Filed: Jul. 20, 1979

[30] Foreign Application Priority Data

Jul. 20, 1978 [JP] Japan .................................. 53-88637

[51] Int. Cl.³ .............................................. C12N 9/04
[52] U.S. Cl. .................................... 435/190; 435/822
[58] Field of Search ................................ 435/190, 822

[56] References Cited

U.S. PATENT DOCUMENTS 4,166,005  8/1979  Masurekar et al. .................. 435/190

Primary Examiner—Lionel M. Shapiro
Attorney, Agent, or Firm—Young & Thompson

[57] ABSTRACT

L-α-glycerophosphate oxidase can be produced by culturing *Aerococcus viridans* IFO-12219 or *Aerococcus viridans* IFO-12317. It is useful for analysis for L-α-glycerophosphate, because it catalyzes the reaction of L-α-glycerophosphate and oxygen to form dihydroxyacetone phosphate and hydrogen peroxide.

1 Claim, 4 Drawing Figures

○—○ : 5mM L-α-GLYCEROL-3-PHOSPHATE (μl)
●—● : 2.5mM H₂O₂

PROCESS FOR THE MANUFACTURE OF L-α-GLYCEROPHOSPHATE OXIDASE

This invention relates to a process for the manufacture of L-α-glycerophosphate oxidase (L-α-glycero-3-phosphate: O₂ oxidoreductase).

L-α-glycerophosphate oxidase is a hitherto-known enzyme which catalyzes a reaction of L-α-glycero-3-phosphate and oxygen to form dihydroxy-acetone-3-phosphate and hydrogen peroxide and has heretofore been derived from a strain of genus Streptococcus, genus Lactobacillus, genus Leuconostoc and genus Pediocuccus. (Japan. Pat. Open, No. 53-72892).

It has now been found that an enzyme L-α-glycerophosphate oxidase can be produced by culturing bacterial strains belonging to genus, for example *Aerococcus viridans* IFO-12219 and IFO-12317.

An object of the present invention is to provide a process for the manufacture of L-α-glycerophosphate oxidase which comprises culturing L-α-glycerophosphate oxidase-producing microorganism belonging to genus Aerococcus in a nutrient culture medium and isolating the L-α-glycerophosphate oxidase thus produced from the cultured medium.

The enzyme L-α-glycerophosphate oxidase is an oxidase which acts on L-α-glycero-3-phosphate as a substrate in biological metabolism, and hence the said enzyme can be used for quantitiative determination of L-α-glycerophosphate, glycerol, glyceride, phosphatidic acid and other phospholipids, and for the measurement of enzyme activity of glycerokinase and the like enzymes optionally in the presence of other enzymes and chromogen reagents. Also the enzyme L-α-glycerophosphate oxidase has utility as a research reagent and diagnostic reagent.

Other objects, features and advantages of the present invention will become apparent from a consideration of the following description, taken in connection with the accompanying drawings, which are graphs illustrating the present invention, and in which more particularly:

Figure 1:
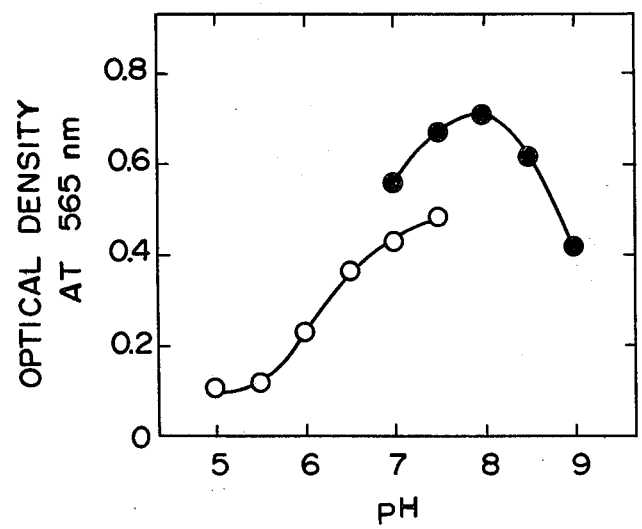
FIG. 1 is a graph of optimum pH of L-α-glycerophosphate oxidase.

An enzyme L-α-glycerophosphate oxidase in this invention is preferably manufactured by culturing, for example, *Aerococcus viridans* IFO-12219 or IFO-12317. IFO-12219 and IFO-12317 were deposited for permanent collection in the Institute for Fermentation, Osaka, Japan, under those numbers.

In an embodiment of the present invention, the above *Aerococcus viridans* IFO-12219 or *Aerococcus viridans* IFO-12317 are cultured in a conventional medium for enzyme production. Cultivation can be effected by conventional liquid culture and submerged aeration culture is preferable for industrial production.

A conventional medium for culturing microorganisms can preferably be used. For the carbon sources, assimilable carbon sources such as glucose, sucrose, lactose, maltose, fructose, molasses, glycerol, pyruvic acid or the like can preferably be used. Assimilable nitrogen sources such as peptone, polypeptone, meat extract, yeast extract, soybean powder, casein hydrolyzate or the like can be used. Various inorganic salts such as phosphates, carbonates, sulfates, salts of magnesium, calcium, potassium, sodium, divalent iron, manganese or zinc can be used.

The culturing temperature can be selected within the range for growth of microbial cells and production of L-α-glycerophosphate oxidase, and is preferably 25°–37° C. The culturing time can be altered depending on conditions and is terminated when L-α-glycerophosphate oxidase production is substantially complete, and is usually 10–48 hours.

To separate L-α-glycerophosphate oxidase from the culture, the cultured mass is filtered or centrifuged to collect the cells, which are disrupted by treatment with mechanical means or enzymes such as lysozyme. Further if necessary L-α-glycerophosphate oxidase is solubilized by adding ethylene-diaminetetraacetic acid (EDTA) and a surfactant such as Triton X-100 (trademark) or Adecatol SO-120 (trademark) to separate the enzyme. The thus-obtained solution of L-α-glycerophosphate oxidase is treated with or without concentration, and thereafter the enzyme is precipitated by salting out with the addition of a soluble salt such as ammonium sulfate, or is precipitated by adding a water-miscible organic solvent such as methanol, ethanol, acetone or isopropanol. Low molecular weight impurities are removed by dialysis. Furthermore purification of L-α-glycerophosphate oxidase is preferably performed by adsorption chromatography or gel filtration. The enzyme solution thus obtained is treated by vacuum concentration, ultra filtration concentration and lyophilization to produce powdered L-α-glycerophosphate oxidase.

L-α-glycerophosphate oxidase of the present invention is assayed as follows and has the following physico-chemical properties:

| Reaction mixture (1.0 ml): | |
|---|---|
| 0.2 M Tris-HCl buffer (pH 8.0) | 0.2 ml |
| peroxidase (0.5 mg/ml, 45 U/ml) | 0.1 ml |
| 0.3%(W/V) 4-aminoantipyrine | 0.1 ml |
| 0.1 M DL-glycero-3-phosphate | 0.1 ml |
| 0.2%(V/V) N,N-dimethylaniline | 0.2 ml |
| distilled water | 0.3 ml |

The above mixture is preincubated at 37° C. for 3 minutes. To the above reaction mixture (1.0 ml) is added L-α-glycerophosphate oxidase solution (20 μl) and the material is incubated at 37° C. for 10 minutes. 0.25%(W/V) sodium lauryl benzene sulfonate (2.0 ml) is added to stop the reaction. The color formed is measured by colorimetric method as 565 nm.

The enzyme activity is calculated by the following equation:

$$\text{Enzyme activity } (U/ml) = (\Delta A/6.0) \times \left(\frac{50}{10}\right)$$

wherein ΔA means absorbency change at 565 nm per 10 minutes.

(2) Enzyme action:

The enzyme catalyzes the oxidative reaction of L-α-glycero-3-phosphate and oxygen to form dihydroxyacetone-3-phosphate and hydrogen peroxide.

(3) Optimum pH:

The effect of pH on L-α-glycerophosphate oxidase activity obtained from *Aerococcus viridans* IFO-12219 is measured in dimethyl glutarate-NaOH buffer (pH 5.9–7.0) and Tris-HCl buffer (pH 7.0–9.0). The results are shown in FIG. 1 in which optimum pH is pH 7.5–8.5.

Figure 2:
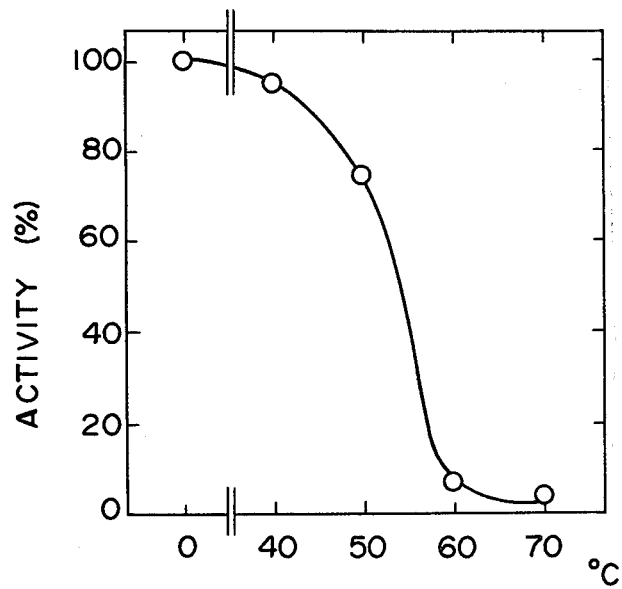
FIG. 2 shows the heat stability of L-α-glycerophosphate oxidase.

(4) Heat stability:

Heat stability of the enzyme obtained from *Aerococcus viridans* IFO-12219 is determined by incubating in 0.1 M dimethyl glutarate-NaOH buffer (pH 7.0) containing the enzyme L-α-glycero-phosphate oxidase at various temperatures in the range of 0°–70° C. for 10 minutes and then cooling with ice. The results are shown in FIG. 2.

Figure 3:
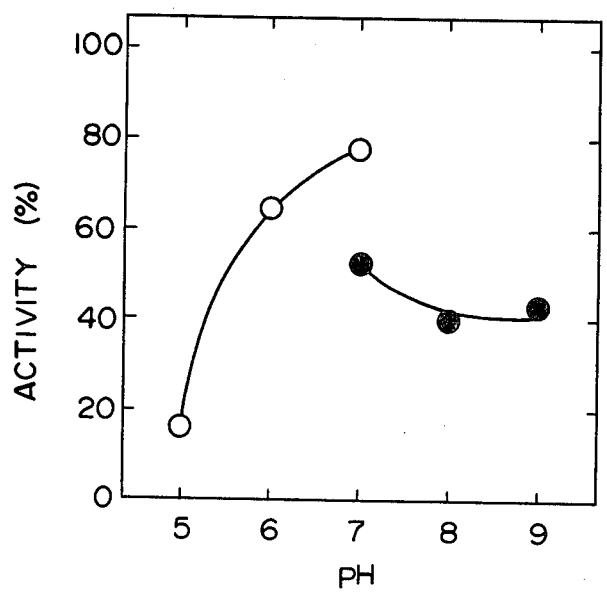
FIG. 3 shows the pH stability of L-α-glycerophosphate oxidase.

(5) pH stability:

To L-α-glycerophosphate oxidase obtained from *Aerococcus viridans* IFO-12219 is added 0.1 M dimethyl glutarate-NaOH buffer to pH 5.0–7.0, and the mixture is allowed to stand for 10 minutes at 45° C. and cooled with ice, and enzyme activity is determined. The results are shown in FIG. 3. The enzyme obtained from *Aerococcus viridans* IFO-12317 has the same characteristics.

The following examples illustrate the embodiments of the present invention but are not to be construed as limiting the invention.

EXAMPLE 1

Two media (pH 7.0) each consisting of glycerol (1.0%), lactose (2.0%), polypeptone (1.0%), yeast extract (1.0%), meat extract (0.5%), $KH_2PO_4$ (0.1%), $K_2HPO_4$ (0.1%), NaCl (0.2%) and $MgSO_4.7H_2O$ (0.05%), with added silicone KS-66 (antifoamer, trademark of Shinetsu Chemical Co.) in a 30 l. jar-fermenter were sterilized at 120° C. for 20 minutes. After cooling, cultured broth (200 ml) of *Aerococcus viridans* IFO-12219 and IFO-12317 previously cultured for 10 hours were transferred thereto, respectively, and cultured at 30° C. for 15 hours. Bacterial cells centrifugally collected at 5000 r.p.m. for 10 minutes, were washed with 10 mM phosphate buffer (pH 7.0, 500 ml) then suspended in lysozyme solution (0.4 mg/ml, 400 ml), and incubated at 37° C. for 60 minutes. The supernatant obtained centrifugally at 5000 r.p.m. for 15 minutes has the following L-α-glycerophosphate oxidase activity.

| Strain | Enzyme activity (u/ml) in cultured medium |
| --- | --- |
| *Aerococcus viridans* IFO-12219 | 0.80 |
| *Aerococcus viridans* IFO-12317 | 0.78 |

EXAMPLE 2

*Aerococcus viridans* IFO-12219 was cultured in the same way as described in Example 1, the thus-obtained cultured medium containing the desired enzyme (420 ml, 16000 u).

To the said enzyme solution was added ammonium sulfate solution at a concentration of 0.24–0.48 saturation. The precipitated material was collected by centrifuge, and was dissolved in 10 mM phosphate buffer (pH 7.0, 50 ml). The solution was dialyzed against 10 mM phosphate buffer (pH 7.0) using a cellulose acetate dialysis tube and was lyophilized to obtain the purified L-α-glycerophosphate oxidase. Recovery: 83.6%.

EXAMPLE 3

Figure 4:
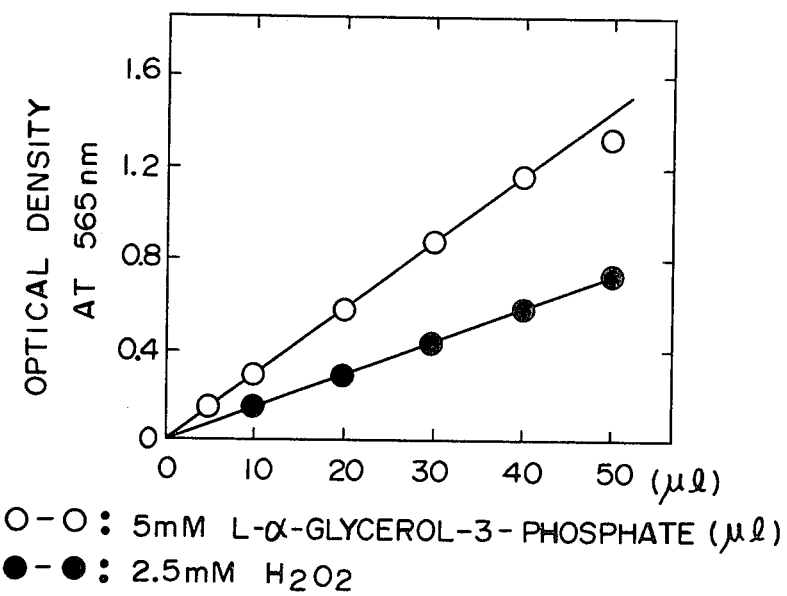
FIG. 4 shows the results of analysis of glycero-3-phosphate using L-α-glycerophosphate oxidase.

5 mM L-α-glycerophosphate (0–50 μl) was used in place of L-glycero-3-phosphate, and there was further added water thereto up to 1.0 ml. To the reaction mixture was added a solution (220 u/ml) of the enzyme obtained in Example 2, and the mixture was incubated at 37° C. for 10 minutes. The reaction was stopped according to the method described in the assay method, then the product was colorimetrically measured at 565 nm. The result is shown in FIG. 4, in which good linearity was obtained up to about absorption at 1.2. The result coincided with the control using $H_2O_2$. In FIG. 4, •–•: 5 mM L-α-glycero-3-phosphate and o–o: 2.5 mM hydrogen peroxide.

What is claimed is:

1. A process for the manufacture of L-α-glycerophosphate oxidase, which comprises culturing L-α-glycerophosphate oxidase-producing microorganism selected from the group consisting of *Aerococcus viridans* IFO-12219 and *Aerococcus viridans* IFO-12317, in a nutrient culture medium, and separating the L-α-glycerophosphate oxidase thus produced from the cultured medium.

* * * * *